United States Patent [19]
Ling

[11] 3,959,362
[45] May 25, 1976

[54] AMMONIUM MERCAPTOALKANESULFONATE SALTS, THEIR PREPARATION, PHOTOGRAPHIC FIXING SOLUTIONS CONTAINING SAME, AND METHOD OF FIXING PHOTOGRAPHIC FILM THEREWITH

[75] Inventor: Hans Gway Ling, Rochester, N.Y.

[73] Assignee: Eastman Kodak Company, Rochester, N.Y.

[22] Filed: Sept. 24, 1973

[21] Appl. No.: 400,100

[52] U.S. Cl. .................... 260/513 R; 260/505 R; 96/56.6; 96/61 R; 96/61 M
[51] Int. Cl.² .......................................... C07C 143/06
[58] Field of Search .............................. 260/513 R

[56] References Cited
UNITED STATES PATENTS

| | | | |
|---|---|---|---|
| 2,799,702 | 7/1957 | Gaertner | 260/513 R |
| 3,438,748 | 4/1969 | Tavernier et al. | 23/315 |

FOREIGN PATENTS OR APPLICATIONS

| | | | |
|---|---|---|---|
| 1,119,721 | 7/1968 | United Kingdom | 260/513 R |
| 1,173,609 | 12/1969 | United Kingdom | 260/513 R |
| 823,447 | 12/1951 | Germany | 260/513 R |

Primary Examiner—James O. Thomas, Jr.
Assistant Examiner—Nicky Chan
Attorney, Agent, or Firm—H. M. Chapin

[57] ABSTRACT

Ammonium mercaptoalkanesulfonate salts having the formula: $HS-R-SO_3^-NH_4^+$ are new salts prepared by a novel process comprising reaction of a thioamide, such as a thioalkanamide or thioarylamide, with a sultone in alcohol. Typical examples comprise reacting thioacetamide with 1,3-propane sultone (for ammonium 3-mercaptopropanesulfonate); with 2,4-butane sultone (for ammonium 3-mercapto-1-methylpropane-sulfonate); and with 1,4-butane sultone (for ammonium 4-mercapto-2-butanesulfonate.) The product can be recovered by precipitation with a nonsolvent for the product such as ether, benzene, or ligroine, followed by filtration. The new ammonium salts in aqueous solution are useful as silver complexing agents for photographic fixing or stabilizing, and are more active than the known alkali metal and guanidinium salts, thus providing a new method of fixing developed silver halide photographic elements.

6 Claims, No Drawings

AMMONIUM MERCAPTOALKANESULFONATE SALTS, THEIR PREPARATION, PHOTOGRAPHIC FIXING SOLUTIONS CONTAINING SAME, AND METHOD OF FIXING PHOTOGRAPHIC FILM THEREWITH

BACKGROUND OF THE INVENTION

1. Field of the Invention

This invention relates to novel compounds useful in photography and in particular to new ammonium mercaptoalkane-sulfonate salts useful as fixing agents for developed silver halide photographic elements, and to their preparation. The invention also concerns novel aqueous fixing solutions containing such compounds, and a novel method of fixing developed silver halide photographic elements.

2. Description of the Prior Art

After an exposed photographic silver halide emulsion is developed and a silver image is produced in the areas of exposure, the silver halide in the unexposed areas is conventionally removed as a soluble silver compound with hypo or other fixing solution if a permanent silver image is desired. It is also possible to fix or stabilize the unexposed and/or undeveloped silver halide by reaction with a compound which forms a silver salt or complex that is colorless or relatively light in color and resistant to print out. A large number of agents form soluble complexes with silver which are sufficiently stable to allow them to function as fixing agents for photographic emulsions. However, in addition to dissolving the silver halides, the fixing agent must form complexes that are stable upon dilution so that insoluble salts will not precipitate during the early stages of washing. Also, the fixing agent should not attack the gelatin of the emulsion or the developed silver to an extent detrimental to the image. Practical considerations in a search for organic compounds suitable as silver complexing agents are:

1. that they exhibit a fast rate of film clearing;
2. that they are readily preparable by a simple process; and
3. that they are reasonably stable toward air.

Accordingly, it is an object of this invention to provide a new class of silver complexing agents.

It is another object to develop a simple 1-step process for the preparation of silver complexing agents.

Still another object is to provide novel aqueous fixing solutions containing the novel agents, and a novel method of fixing developed photographic film therewith, which exhibit a faster rate of film clearing than other agents.

Another object is to provide silver complexing agents as silver halide solvents, which are resistant to air oxidation.

Additional objects and advantages of the present invention will become apparent from a consideration of the following specification and appended claims.

DETAILED DESCRIPTION

These and other objects of the present invention are accomplished with new ammonium mercaptoalkane-sulfonate salts having the following formula:

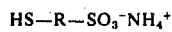

wherein R is an alkylene group, either linear or branched chain, having from 3 to 8 carbon atoms, and advantageously 3 to 4 carbon atoms.

Suitable alkylene groups are:
trimethylene
1-methyltrimethylene
2-methyltrimethylene
2,2-dimethyltrimethylene
2-methyltetramethylene
3-methyltetramethylene
3,3-dimethyltrimethylene
2,3,3-trimethyltrimethylene
2,2,3,3-tetramethyltrimethylene
pentamethylene
4-methyltetramethylene
2,4-dimethyltetramethylene
2,2,4,4-tetramethyltetramethylene
1,3-dimethyltrimethylene
1,1,3-trimethyltrimethylene
1,3,3-trimethyltrimethylene
1,2,3,3-tetramethyltrimethylene
1,2,2,3,3-pentamethyltrimethylene Particularly advantageous salts of the present invention are:
Ammonium 3-mercapto-1-propanesulfonate
Ammonium 4-mercapto-2-butanesulfonate
Ammonium 3-mercapto-2-methyl-1-propane-sulfonate
Ammonium 3-mercapto-1-methylpropanesulfonate
Ammonium 2,2-dimethyl-3-mercapto-1-propanesulfonate
Ammonium 4-mercapto-2-methyl-1-butanesulfonate
Ammonium 4-mercapto-3-methyl-1-butanesulfonate
Ammonium 3-mercapto-3-methyl-1-butanesulfonate
Ammonium 2,3-dimethyl-3-mercapto-1-butanesulfonate
Ammonium 3-mercapto-2,2,3-trimethyl-1-butanesulfonate
Ammonium 5-mercapto-1-pentanesulfonate
Ammonium 4-mercapto-1-pentanesulfonate
Ammonium 4-mercapto-2-methyl-1-pentanesulfonate
Ammonium 4-mercapto-2,2,4-trimethyl-1-pentanesulfonate
Ammonium 4-mercapto-2-pentanesulfonate
Ammonium 4-mercapto-2-methyl-2-pentanesulfonate
Ammonium 4-mercapto-4-methyl-2-pentanesulfonate
Ammonium 3,4-dimethyl-4-dimethyl-4-mercapto-2-pentanesulfonate
Ammonium 4-mercapto-3,3,4-trimethyl-2-pentanesulfonate The salts of the present invention can be prepared by a process comprising heating a thioamide, such as a thioalkanamide or a thioarylamide, with a sultone in a suitable alcohol solvent (desirably at 60°–150°C, conveniently at reflux).

I. 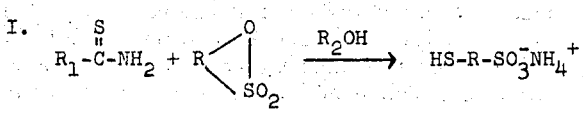

wherein $R_1$ is aryl, or a linear alkyl radical having 1 to 10 carbon atom (preferably 1 to 4 C) or a branched chain alkyl radical having 3 to 10 carbon atoms (preferably having 3 to 4 carbon atoms) and $R_2$ is a linear alkyl radical having 1 to 6 carbon atoms, or a branched chain alkyl radical having 3 to 6 carbon atoms; and wherein R is an alkylene group as described above.

Useful thioamides include:

thioacetamide
thiopropionamide
thioisopropionamide
thiobutyramide
thiovaleramide
thiohexanamide
thioheptanamide
thiooctanamide
thio-2-ethylhexanamide
thiononanamide
thiodecanamide
thiobenzamide
thio-p-toluamide Useful sultones include:
3-Hydroxy-1-propanesulfonic acid, gamma sultone (commonly called 1,3-propanesultone)
4-Hydroxy-2-butanesulfonic acid, gamma sultone (commonly called 2,4-butanesultone)
3-Hydroxy -2-methyl-1-propanesulfonic acid, gamma sultone
2,2-Dimethyl-3-hydroxy-1-propanesulfonic acid, gamma sultone
4-Hydroxy-2-methyl-1-butanesulfonic acid, delta sultone
4-Hydroxy-3-methyl-1-butanesulfonic acid, delta sultone
3-Hydroxy-3-methyl-1-butanesulfonic acid, gamma sultone
2,3-Dimethyl-3-hydroxy-1-butanesulfonic acid, gamma sultone
3-Hydroxy-2,2,3-trimethyl-1-butanesulfonic acid, gamma sultone
5-Hydroxy-1-pentanesulfonic acid, epsilon sultone
4-Hydroxy-1-pentanesulfonic acid, delta sultone
4-Hydroxy-2-methyl-1-pentanesulfonic acid, delta sultone
4-Hydroxy-2,2,4-trimethyl-1-pentanesulfonic acid, delta sultone
4-Hydroxy-2-pentanesulfonic acid, gamma sultone
4-Hydroxy-2-methyl-2-pentanesulfonic acid, gamma sultone
4-Hydroxy-4-methyl-2-pentanesulfonic acid, gamma sultone
3,4-dimethyl-4-hydroxy-2-pentanesulfonic acid, gamma sultone
4-Hydroxy-3,3,4-trimethyl-2-pentanesulfonic acid, gamma sultone Suitable solvents are for example monohydric alcohols or mixtures of two or more such alcohols, having from 1 to 6 carbon atoms. The time required to complete the reaction is dependent on the reactivity of the sultone and the boiling point of the solvent employed. Low boiling alcohols such as methanol or ethanol or mixtures thereof are used to advantage with highly reactive sultones such as 1,3-propane sultone and 2,4-butane sultone. If a less active sultone is used, there may be employed a longer reaction time, or a higher boiling alcohol to assure a higher reaction temperature.

Upon completion of the reaction, the ammonium mercaptoalkanesulfonate salt is conveniently isolated by adding a "non-solvent" to the concentrated reaction liquors to precipitate the product which is then filtered out and recovered. By a "non-solvent" is meant a non polar organic liquid which is soluble in the polar alcohol reaction solvents, but which will not dissolve the ammonium salt product. In a preferred embodiment, the nonsolvent is anhydrous diethyl ether. Other useful nonsolvents are aliphatic hydrocarbons such as ligroine. Other non polar organic liquids such as common halogenated solvents, eg. methylene chloride and chloroform, and aromatic liquids such as benzene, toluene, xylene, and chlorobenzene can be used.

Since Reaction I is equimolar with respect to the thioamide and the sultone, the ratio of the reactants present is not critical, as the reactant which is present in the least amount will be determinative of the moles of products formed. The solvent can be present in a ratio of 10 to 100 moles per total moles of reactants, and preferably in a ratio of 20 to 25. The nonsolvent should be used in an amount sufficient to precipitate all the product, and is generally about the same in volume as the alcohol solvent employed.

The ammonium salts of the present invention are particularly useful as silver complexing agents in photographic fixing because they exhibit a faster rate of film clearing than corresponding alkali metal salts or guanidinium salts. Additionally, they are readily prepared by a simple process and are reasonably stable toward air.

EXAMPLE 1

Preparation of ammonium 3-mercaptopropanesulfonate ($C_3H_{11}NO_3S_2$)

A solution of 50.0 grams of thioacetamide and 81.5 grams of 1,3-propane sultone in 700 ml of methanol is refluxed at atmospheric pressure for 10 minutes. The reaction mixture is then concentrated by evaporation of solvent to 200 ml, and 600 ml of anhydrous diethyl ether is added. A white precipitate is formed, is collected by filtration and then is dissolved in 350 ml of ethanol. After drying and decolorizing with 4A molecular sieves* and charcoal, addition of anhydrous diethyl ether to the filtered solution, and refiltration, the yield is 59.7 g (50% of theoretical) of shiny white crystals of ammonium 3-mercaptopropanesulfonate having a melting point of 160°C. $C_3H_{11}NO_3S_2$ Calculated % C, 20.8; H, 6.4; N, 8.1

Found % C. 21.9; H, 6.1; N, 8.0

*An activated crystalline metal alumino-silicate sold by the Linde Division of Union Carbide Corporation. Pellets have a diameter of 1/16 inch and a bulk density of 30.

EXAMPLE 2

Preparation of ammonium 3-mercapto-1-methylpropanesulfonate

A solution of 15.0 g of thioacetamide and 27.2 g of 2,4-butane sultone in 250 ml of methanol is refluxed at atmospheric pressure for 30 minutes. The small amount of solid residue is removed by filtration, the filtrate is evaporated to a thick oil-like consistency, is dissolved in 200 ml of ethanol, and then dried and decolorized over 4A molecular sieves and charcoal. 50 ml of anhydrous diethyl ether are added to the solution, and 15.0 g (40% of theoretical) of hygroscopic white solid ammonium-3-mercapto-1-methylpropanesulfonate precipitate out and are recovered by refiltration; m.p. 90°–150°C (decomposes). The compound gives a strongly positive mercaptan test and releases ammonia gas when treated with base. Infra-red and nmr spectra confirm the structure.

EXAMPLE 3

Preparation of ammonium 4-mercapto-2-butanesulfonate

Thioacetamide (7.5 g) and 1,4-butane sultone (13.6 g) are dissolved in 250 ml of 1:1 mixture of methanol and ethanol. The solution is refluxed at atmospheric pressure for 8 hours and then decolorized with charcoal and dried over 4A molecular sieves. After concentration to 150 ml volume, 500 ml of anhydrous ether are added. The resulting shiny white crystals are filtered off, weight 5.0 g (27% of theoretical), sintered at 134°–135°C. They give a strongly positive mercaptan test and good infra-red and nmr spectra which are consistent with the assigned structure ammonium 4-mercapto-2-butanesulfonate.

The following examples give a comparison of an ammonium compound of the present invention with sodium and guanidinium counterparts and serve to illustrate the improved film clearing rate achieved with the novel ammonium compounds of the present invention which make them useful for fixing the images on developed photographic film.

EXAMPLE 4

Separate 3% aqueous solutions are made of sodium and ammonium 3-mercaptopropanesulfonates. A strip of unexposed photographic film is inserted in each solution and the time required to remove all of the silver halide from the immersed portions (the clearing time) is determined. The results are shown in the Table A below.

Table A

| | Time For Film Clearing | |
|---|---|---|
| | $Na^+$ Salt | $NH_4^+$ Salt |
| Without base added | 870 seconds | 510 seconds |
| With base added* | 260 seconds | 50 seconds |

*1 drop of 10% aqueous NaOH in 3 ml of solution to raise the pH to near neutral and thus to speed up the reaction.

EXAMPLE 5

Separate 2% aqueous solutions are made of guanidinium and ammonium 3-mercapto-1-methylpropanesulfonate. One drop of 10% aqueous NaOH is added, and clearing times are determined as in Example 4. The ammonium salt gives a clearing time of 78 seconds in contrast to 175 seconds for the guanidinium salt.

From the foregoing results, it is evident that the novel compounds of the present invention give surprisingly improved results over the corresponding salts of sodium and guanidinium when used as aqueous photographic fixing solutions. Normally one would expect the sodium and guanidinium salts to give faster clearing times because of their basic nature, whereas the novel ammonium compounds are acidic.

The invention has been described in detail with particular reference to preferred embodiments thereof, but it will be understood that variations and modifications can be effected within the spirit and scope of the invention.

I claim:

1. A method for preparing an ammonium mercaptoalkanesulfonate salt which comprises reacting at about 60° to 150°C a thioamide and a sultone dissolved in an alcohol solvent wherein said alcohol solvent is present in a ratio of 10 to 100 moles per total moles of reactants, a. said thioamide having the formula

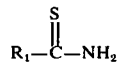

wherein $R_1$ is an alkyl radical having 1 to 4 carbon atoms, b. said sultone having the formula

wherein R is an alkylene group having 3 to 5 carbon atoms, c. said alcohol solvent having the formula $R_2OH$ wherein $R_2$ is an alkyl radical having 1 to 6 carbon atoms.

2. A method in accordance with claim 1 wherein $R_1$ is methyl.

3. A method in accordance with claim 1 wherein said alcohol solvent is methanol, ethanol, or a mixture of methanol with ethanol.

4. A method in accordance with claim 3 wherein said thioamide is thioacetamide.

5. A method in accordance with claim 1, comprising adding said thioamide and said sultone in equimolar proportions.

6. A method for preparing an ammonium mercaptoalkane sulfonate salt in accordance with claim 1 further comprising precipitating the resulting ammonium mercaptoalkane sulfonate salt by adding to the reaction mixture a non polar organic liquid which is soluble in the alcohol solvent but which will not dissolve said ammonium mercaptoalkanesulfonate salt, said non polar liquid being diethylether, ligroine, methylene chloride, chloroform, benzene, toluene, xylene, or chlorobenzene.

* * * * *

UNITED STATES PATENT AND TRADEMARK OFFICE
CERTIFICATE OF CORRECTION

PATENT NO. : 3,959,362
DATED : May 25, 1976
INVENTOR(S) : Hans Gway Ling

It is certified that error appears in the above–identified patent and that said Letters Patent are hereby corrected as shown below:

Column 2, line 46, delete "4-dimethyl", second occurrence, so the compound reads:

"Ammonium 3,4-dimethyl-4-mercapto-2-pentanesulfonate"

Signed and Sealed this

Twenty-sixth Day of October 1976

[SEAL]

Attest:

RUTH C. MASON
*Attesting Officer*

C. MARSHALL DANN
*Commissioner of Patents and Trademarks*